US009826885B2

(12) United States Patent
Ono et al.

(10) Patent No.: US 9,826,885 B2
(45) Date of Patent: Nov. 28, 2017

(54) ENDOSCOPE SYSTEM

(71) Applicant: OLYMPUS CORPORATION, Tokyo (JP)

(72) Inventors: Wataru Ono, Hachioji (JP); Satoshi Takekoshi, Hachioji (JP); Shunji Takei, Hachioji (JP); Kenji Yamazaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/971,079

(22) Filed: Dec. 16, 2015

(65) Prior Publication Data

US 2016/0100741 A1    Apr. 14, 2016

Related U.S. Application Data

(63) Continuation of application No. PCT/JP2014/069604, filed on Jul. 24, 2014.

(30) Foreign Application Priority Data

Aug. 1, 2013    (JP) .................................. 2013-160736

(51) Int. Cl.
A61B 1/04    (2006.01)
A61B 1/06    (2006.01)
(Continued)

(52) U.S. Cl.
CPC .......... *A61B 1/00006* (2013.01); *A61B 1/045* (2013.01); *A61B 1/05* (2013.01);
(Continued)

(58) Field of Classification Search
CPC .......... H04N 5/00; H04N 5/232–5/247; G02B 23/24–23/26
See application file for complete search history.

(56) References Cited

U.S. PATENT DOCUMENTS 6,448,561 B1 *   9/2002  Kaifu ..................... H04N 5/235
                                                250/370.09
6,529,768 B1 *   3/2003  Hakamata .......... A61B 1/00009
                                                600/310

(Continued)

FOREIGN PATENT DOCUMENTS

CN    102334971 A    2/2012
CN    103140161 A    6/2013

(Continued)

OTHER PUBLICATIONS

International Search Report dated Oct. 28, 2014 issued in PCT/JP2014/069604.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope system includes: an illumination unit configured to irradiate a visual field area with illumination light that produces return light from a specific substance; a sensor unit having a two-dimensional surface on which a plurality of pixels is arranged for receiving the return light from the visual field area and photoelectrically converting the return light to generate electrical signals; a reading unit configured to read out the electrical signals per a specified frame cycle; a reset pulse generation unit configured to generate reset pulses for releasing electric charges accumulated in the plurality of pixels; a reset pulse controller configured to adjust timing of generating the reset pulses such that a plurality of frame cycles is included in a period between generation of two consecutive reset pulses; and an illumination controller configured to cause the illumination unit to (Continued)

emit the illumination light in each of the plurality of frame cycles.

3 Claims, 11 Drawing Sheets

(51) Int. Cl.
    *A61B 1/045*      (2006.01)
    *A61B 1/00*      (2006.01)
    *A61B 1/05*      (2006.01)
    *G02B 23/24*      (2006.01)
    *H04N 5/235*      (2006.01)
    *H04N 5/353*      (2011.01)
    *A61B 1/313*      (2006.01)
    *H04N 5/225*      (2006.01)

(52) U.S. Cl.
    CPC .......... *A61B 1/0638* (2013.01); *A61B 1/0661* (2013.01); *A61B 1/3132* (2013.01); *G02B 23/2484* (2013.01); *H04N 5/2353* (2013.01); *H04N 5/2354* (2013.01); *H04N 5/3532* (2013.01); *A61B 1/0684* (2013.01); *H04N 2005/2255* (2013.01)

(56) References Cited

U.S. PATENT DOCUMENTS

| | | | |
|---|---|---|---|
| 7,064,828 B1* | 6/2006 | Rovira | G01J 3/447 356/369 |
| 8,540,626 B2 | 9/2013 | Seto et al. | |
| 8,545,399 B2 | 10/2013 | Takei et al. | |
| 2003/0001951 A1* | 1/2003 | Tsujita | A61B 1/043 348/65 |
| 2007/0097294 A1* | 5/2007 | Tsukimura | A61B 1/04 349/110 |
| 2007/0147810 A1* | 6/2007 | Sugimoto | A61B 1/04 396/17 |
| 2010/0069713 A1 | 3/2010 | Endo et al. | |
| 2013/0150713 A1 | 6/2013 | Takei et al. | |
| 2013/0201315 A1 | 8/2013 | Takei et al. | |
| 2013/0300849 A1* | 11/2013 | Ono | A61B 1/00006 348/68 |
| 2013/0307951 A1* | 11/2013 | Ono | H04N 5/2354 348/68 |
| 2014/0203170 A1* | 7/2014 | Ono | G02B 26/02 250/208.1 |

FOREIGN PATENT DOCUMENTS

| | | |
|---|---|---|
| EP | 2 601 881 A1 | 6/2013 |
| JP | 2010-068992 A | 4/2010 |
| JP | 2011-206336 A | 10/2011 |
| JP | 2012-143319 A | 8/2012 |
| WO | WO 2012/172908 A1 | 12/2012 |
| WO | WO 2012/176561 A1 | 12/2012 |

OTHER PUBLICATIONS

Extended Supplementary European Search Report dated Feb. 17, 2017 in related European Patent Application No. 14 83 2959.2.
Chinese Office Action dated Nov. 4, 2016 in related Chinese Patent Application No. 201480035770.8.

\* cited by examiner

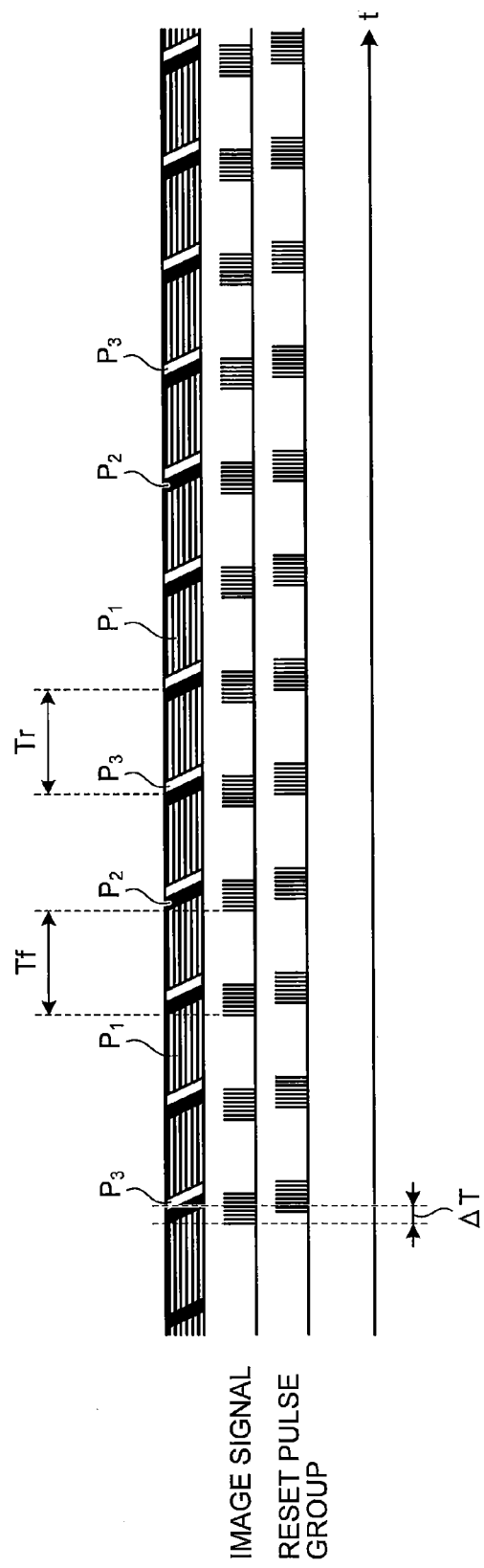

ENDOSCOPE SYSTEM

CROSS-REFERENCE TO RELATED APPLICATIONS

This application is a continuation of PCT international application Ser. No. PCT/JP2014/069604 filed on Jul. 24, 2014 which designates the United States, incorporated herein by reference, and which claims the benefit of priority from Japanese Patent Application No. 2013-160736, filed on Aug. 1, 2013, incorporated herein by reference.

BACKGROUND

1. Technical Field

The disclosure relates to an endoscope system including an imaging element for outputting, as pixel information, an electrical signal after photoelectric conversion from a pixel arbitrarily specified as a reading target, among a plurality of pixels for imaging.

2. Related Art

Conventionally, in the medical field, endoscope systems have been used when an observation of an organ of a subject such as a patient is performed. The endoscope systems include an insertion unit that is inserted into a body cavity of the subject, an imaging unit that is provided at a distal end of the insertion unit and captures an in-vivo image, and a display unit that can display the in-vivo image captured by the imaging unit. To acquire the in-vivo image, using the endoscope systems, the insertion unit is inserted into the body cavity of the subject, and then predetermined illumination light is irradiated from the distal end of the insertion unit, and the imaging unit captures the image.

In recent years, complementary metal oxide semiconductor (CMOS) image sensors have been applied as the imaging unit (see Japanese Laid-open Patent Publication No. 2010-68992, for example). In the CMOS image sensors, the way of reading out the pixel information based on electric charges accumulated in the pixels can be arbitrarily set. Therefore, the CMOS image sensor can perform a wider variety of imaging than a charge coupled device (CCD) image sensor that reads out all of the pixels at the same time.

FIG. 12 is a diagram schematically illustrating an outline of an image acquisition method performed by a conventional endoscope system using a CMOS image sensor. In FIG. 12, periods $P_1$, $P_2$, and $P_3$ respectively represent an exposure period of each horizontal line, a transfer period of an image signal after exposure, and a reset period in which a reset signal occurs. Further, in FIG. 12, a frame cycle Tf and a reset cycle Tr are equal.

If the CMOS image sensor is employed, an image signal and a reset pulse group are transferred or occur in each horizontal line. Therefore, a time difference in signal occurrence is caused between a first horizontal line and a last horizontal line ($\Delta T$ of FIG. 12).

SUMMARY

In some embodiments, an endoscope system includes: an illumination unit configured to irradiate a visual field area with illumination light that produces return light from a specific substance; a sensor unit having a two-dimensional surface on which a plurality of pixels is arranged for receiving the return light from the visual field area and photoelectrically converting the return light to generate electrical signals, the sensor unit being configured to sequentially read out the electrical signals generated by the plurality of pixels, as image information; a reading unit configured to read out the electrical signals per a specified frame cycle; a reset pulse generation unit configured to generate reset pulses for releasing electric charges accumulated in the plurality of pixels; a reset pulse controller configured to adjust timing of generating the reset pulses such that a plurality of frame cycles is included in a period between generation of two consecutive reset pulses; and an illumination controller configured to cause the illumination unit to emit the illumination light in each of the plurality of frame cycles present between the generation of one reset pulse and the generation of a next reset pulse.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a diagram schematically illustrating an outline of an image acquisition method performed by a conventional endoscope system.

DETAILED DESCRIPTION

Hereinafter, modes for carrying out the present invention (hereinafter, referred to as "embodiment(s)") will be described with reference to the appended drawings. Note that the drawings to be referred in the following description are schematic drawings, and when the same object is illustrated in different drawings, dimensions, scales, and the like may differ.

First Embodiment

Figure 1:
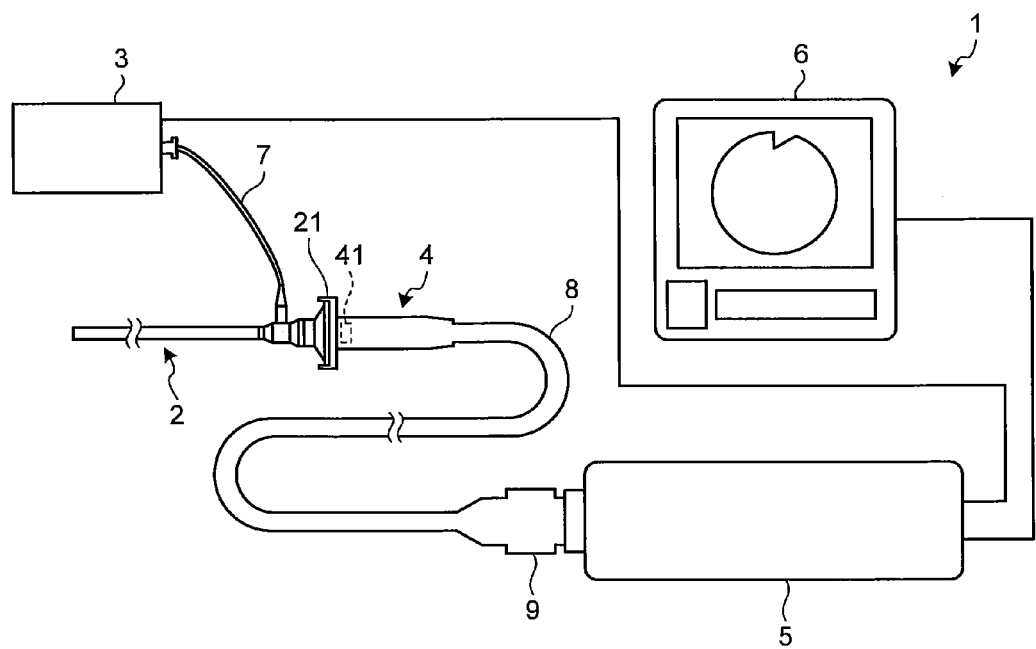
FIG. 1 is a diagram illustrating a schematic configuration of an endoscope system according to a first embodiment of the present invention.

FIG. 1 is a diagram illustrating a schematic configuration of an endoscope system according to a first embodiment of the present invention. An endoscope system 1 illustrated in FIG. 1 includes an insertion unit 2, a light source device 3, a camera head unit 4, a control device 5, a display device 6, a light guide 7, a cable assembly 8, and a connector 9. The endoscope system 1 is a rigid mirror used in a laparoscopic surgical operation (endoscopic operation) or the like by being inserted into an abdominal cavity of a subject.

The insertion unit 2 is rigid and has a long and narrow shape, and includes therein an optical system that is configured to be inserted into a body cavity, a pipeline, or the like, and collects light of an object image.

The light source device 3 supplies irradiation light to the insertion unit 2 through the light guide 7.

The camera head unit 4 is detachably attached to an eyepiece unit 21 provided at a proximal end of the insertion unit 2. The camera head unit 4 includes an imaging element 41 that forms the object image collected by the insertion unit 2, photoelectrically converts the object image into an electrical signal, and outputs the electrical signal.

The control device 5 has a function to perform image processing on the image acquired by the camera head unit 4, and has a function to centrally control an operation of the entire endoscope system 1.

The display device 6 displays the image on which the image processing is performed by the control device 5.

The cable assembly 8 is formed of a plurality of bundled signal lines, and one end is connected to the camera head unit 4 and the other end is provided with the connector 9. The plurality of signal lines included in the cable assembly 8 includes a signal line that transmits the image signal output by the imaging element 41 to the control device 5, a signal line that transmits a control signal output by the control device 5 to the imaging element 41, and the like.

The connector 9 is detachably connected to the control device 5.

Figure 2:
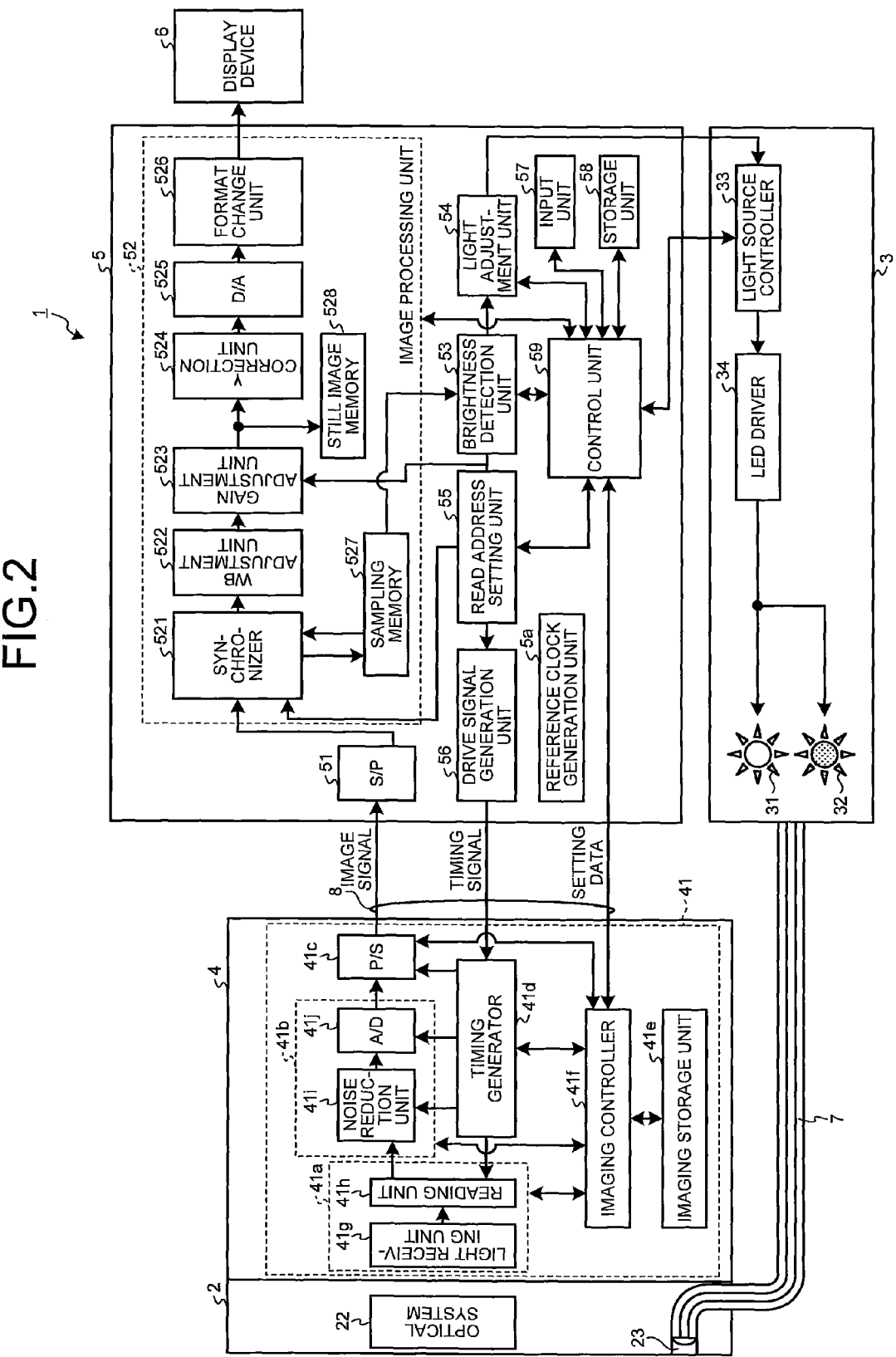
FIG. 2 is a block diagram illustrating functional configurations of principal parts of the endoscope system according to the first embodiment of the present invention.

FIG. 2 is a block diagram illustrating functional configurations of principal parts of the endoscope system 1. First, a configuration of the insertion unit 2 will be described. The insertion unit 2 includes an optical system 22 for light collecting and an illumination lens 23 provided at a distal end of the light guide 7.

Next, a configuration of the light source device 3 will be described. The light source device 3 has a function as an illumination unit that can emit illumination light to a visual field area, the illumination light causing return light from a specific substance. To be specific, the light source device 3 includes a white light source 31, a special light source 32, a light source controller 33, and a light emitting diode (LED) driver 34.

The white light source 31 is made of a white LED, and generates white illumination light.

The special light source 32 generates excitation light for generating fluorescence having a predetermined wavelength. Note that, as the special light generated by the special light source 32, more generally, any light may be used as long as the light causes return light from a specific substance. An example of such light includes infrared light.

The light source controller 33 controls a current amount to be supplied to the white light source 31 or the special light source 32, according to a light source synchronization signal transmitted from a light adjustment unit 54 (described below) of the control device 5 and a control signal from a control unit 59 (described below).

The LED driver 34 causes the white light source 31 or the special light source 32 to generate light, by supplying a current to the white light source 31 or the special light source 32 under control of the light source controller 33. The light generated by the white light source 31 or the special light source 32 irradiates an outside from the distal end of the insertion unit 2 through the light guide 7.

Next, a configuration of the imaging element 41 will be described. The imaging element 41 includes a sensor unit 41a, an analog front-end (AFE) unit 41b, a P/S converter 41c, a timing generator 41d, an imaging storage unit 41e, and an imaging controller 41f. The sensor unit 41a photoelectrically converts the light from the optical system 22 of the insertion unit 2 and outputs an electrical signal. The analog front-end unit 41b applies noise removal and A/D conversion to the electrical signal output from the sensor unit 41a. The P/S converter 41c performs parallel-serial conversion on a digital signal output by the analog front-end unit 41b. The timing generator 41d generates a drive timing pulse of the sensor unit 41a, and pulses for various types of signal processing in the analog front-end unit 41b and the P/S converter 41c. The imaging storage unit 41e stores information such as setting data of the imaging element 41. The imaging controller 41f controls an operation of the imaging element 41. The imaging element 41 is a complementary metal oxide semiconductor (CMOS) image sensor.

The sensor unit 41a includes a light receiving unit 41g and a reading unit 41h. The light receiving unit 41g has a plurality of pixels arranged on a two-dimensional surface in a matrix manner, each of the pixels including a photodiode that accumulates an electric charge according to a light amount, and an amplifier that amplifies the electric charge accumulated by the photodiode. The reading unit 41h reads, as image information, an electrical signal generated by a pixel arbitrarily set as a reading target, among the plurality of pixels of the light receiving unit 41g. In a case where the white light source 31 generates white light, the light receiving unit 41g is provided with individual color filters of RGB for each pixel, and can acquire a color image. In contrast, in a case where the special light source 32 generates fluorescence excitation light as the special light, the light receiving unit 41g is provided with a filter that cuts the excitation light and transmits only fluorescence. As described above, the filters provided in the light receiving unit 41g are different depending on the type of the light source to be used, of the white light source 31 and the special light source 32. Typically, the camera head unit 4 is replaced according to the type of the light source. However, it may be configured to replace the filters in the light receiving unit 41g.

The analog front-end unit 41b includes a noise reduction unit 41i that reduces a noise component included in a signal, and an A/D converter 41j that performs A/D conversion of the signal with a reduced noise. The noise reduction unit 41i reduces the noise, using a correlated double sampling method, for example. Note that an auto gain control (AGC) circuit that automatically adjusts a gain of the signal and maintains an output level on a constant basis may be provided between the noise reduction unit 41i and the A/D converter 41j.

The timing generator 41d has a function as a reset pulse generation unit that sequentially generates reset pulses for releasing the electric charges accumulated by the plurality of pixels of the light receiving unit 41g.

The imaging storage unit 41e is a register that stores various types of setting data and control parameters transmitted from the control unit 59 of the control device 5.

The imaging controller 41f controls an operation of the imaging element 41, according to the setting data received from the control device 5. The imaging controller 41f includes a central processing unit (CPU) and the like. The imaging controller 41f transmits to the timing generator 41d a signal for adjusting timing of generating reset pulses such that at least a part of a plurality of frames of an image is included in a period between the generation of two consecutive reset pulses. In this sense, in the embodiment, the imaging controller 41f has at least a part of a function of a reset pulse controller.

Next, a configuration of the control device 5 will be described. The control device 5 includes an S/P converter 51, an image processing unit 52, a brightness detection unit 53, the light adjustment unit 54, a read address setting unit 55, a drive signal generation unit 56, an input unit 57, a storage unit 58, the control unit 59, and a reference clock generation unit 5a.

The S/P converter 51 performs serial-parallel conversion on an image signal (digital signal) received from the camera head unit 4.

The image processing unit 52 generates an in-vivo image displayed by the display device 6, based on the image signal in a parallel form output from the S/P converter 51. The image processing unit 52 includes a synchronizer 521, a white balance (WB) adjustment unit 522, a gain adjustment unit 523, a γ correction unit 524, a D/A converter 525, a format change unit 526, a sampling memory 527, and a still image memory 528.

The synchronizer 521 inputs the image signal, which has been input as the image information, to three memories (not illustrated) provided in each pixel, holds values of the respective memories while sequentially updating the values, corresponding to an address of the pixel of the light receiving unit 41g, the address having been read by the reading unit 41h, and synchronizes the image signals of these three memories, as an RGB image signal. The synchronizer 521 sequentially outputs the synchronized image signals to the white balance adjustment unit 522, and outputs a part of the image signals to the sampling memory 527, as a signal for image analyses such as brightness detection.

The white balance adjustment unit 522 adjusts white balance of the image signal.

The gain adjustment unit 523 performs gain adjustment of the image signal. The gain adjustment unit 523 outputs the image signal subjected to the gain adjustment to the γ correction unit 524, and outputs a part of the image signals to the still image memory 528, as a signal for still image display, enlarged image display, or enhanced image display.

The γ correction unit 524 performs gray level correction (γ correction) on the image signal corresponding to the display device 6.

The D/A converter 525 converts the image signal subjected to the gray level correction output by the γ correction unit 524 into an analog signal.

The format change unit 526 changes the image signal converted into the analog signal to a signal in a file format for moving image, and outputs the signal to the display device 6. As the file format, an AVI format, an MPEG format, or the like can be applied.

The brightness detection unit 53 detects a brightness level corresponding to each pixel, from the image signal held in the sampling memory 527, records the detected brightness level in a memory provided inside the brightness detection unit 53, and outputs the detected brightness level to the control unit 59. Further, the brightness detection unit 53 calculates a gain adjusted value and a light irradiation amount, based on the detected brightness level, outputs the gain adjusted value to the gain adjustment unit 523, and outputs the light irradiation amount to the light adjustment unit 54.

The light adjustment unit 54 sets the type of the light generated by the light source device 3, a light amount, light emission timing, and the like, based on the light irradiation amount calculated by the brightness detection unit 53 under control of the control unit 59, and transmits a light source synchronization signal including the set conditions to the light source device 3.

The read address setting unit 55 has a function to set pixels to be read and a readout order in the light receiving unit of the sensor unit 41a. That is, the read address setting unit 55 has a function to set the addresses of the pixels of the sensor unit 41a, the pixels being read out by the analog front-end unit 41b. Further, the read address setting unit 55 outputs address information of the set pixels to be read to the synchronizer 521.

The drive signal generation unit 56 generates a drive timing signal for driving the imaging element 41, and transmits the drive timing signal to the timing generator 41d through a predetermined signal line included in a cable assembly 256. This timing signal includes the address information of the pixels to be read.

The input unit 57 receives inputs of various signals such as an operation instruction signal that instructs an operation of the endoscope system 1.

The storage unit 58 is realized using a semiconductor memory such as a flash memory or a dynamic random access memory (DRAM). The storage unit 58 stores various programs for operating the endoscope system 1 and data including various parameters necessary for the operation of the endoscope system 1.

The control unit 59 includes a CPU and the like, and performs drive control of configuration units including the camera head unit 4 and the light source device 3, input/output control of information to/from the configuration units, and the like. The control unit 59 transmits setting data for imaging control to the imaging element 41 through a predetermined signal line included in the cable assembly 256. Here, the setting data includes an imaging speed (frame rate) of the imaging element 41, instruction information that instructs a readout speed of the pixel information from an arbitrary pixel of the sensor unit 41a, transmission control information of the pixel information read out by the analog front-end unit 41b, and the like.

The reference clock generation unit 5a generates a reference clock signal that serves as a reference of an operation of each configuration unit of the endoscope system 1, and supplies the generated reference clock signal to the each configuration unit of the endoscope system 1.

Next, a configuration of the display device 6 will be described. The display device 6 has a function to receive and display the in-vivo image generated by the control device 5, from the control device 5. The display device 6 includes a display such as a liquid crystal display, or an organic electro luminescence (EL) display.

Figure 3:
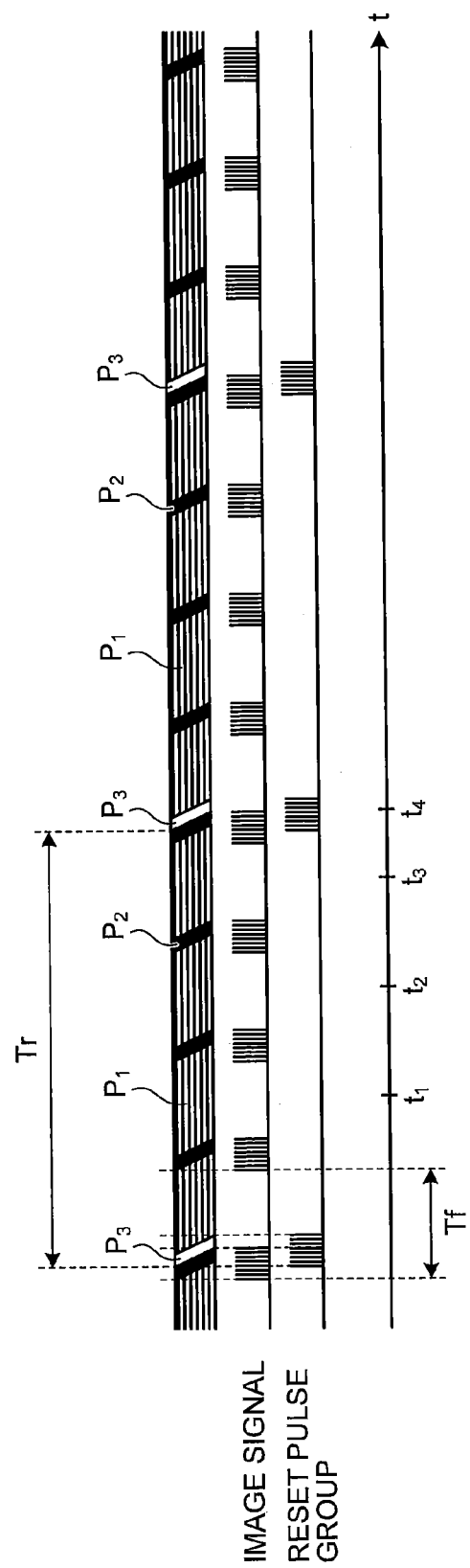
FIG. 3 is a diagram schematically illustrating an outline of an image acquisition method performed by the endoscope system according to the first embodiment of the present invention.

FIG. 3 is a diagram schematically illustrating an outline of an image acquisition method performed by the endoscope system 1 having the above configurations. As described above, the imaging element 41 is a CMOS image sensor, and when a plurality of frames is continuously captured, readout of the accumulated electric charges is sequentially performed in every one horizontal line. Therefore, a time gap in readout timing is caused between the horizontal line (the uppermost portion on the screen in the case of FIG. 3) first read out by the reading unit 41h, and the horizontal line (the lowermost portion on the screen in the case of FIG. 3) lastly read out by the reading unit 41h. In the description below, assume that the light source device 3 continuously generates the same illumination light (for example, the fluorescence excitation light).

In the imaging element 41, after exposure is sequentially performed in every horizontal line during an exposure period $P_1$, the reading unit 41h reads out the electric change accumulated in each pixel of the light receiving unit 41g by exposure, and transfers the read electric change to the analog front-end unit 41b (in a transfer period $P_2$).

The imaging controller 41f resets the electric charges accumulated by the light receiving unit 41g, in a longer reset cycle Tr (>Tf) than a frame cycle Tf, without resetting the electric charges every time a cycle of a set of the exposure and the transfer is terminated like a conventional case. Here, the imaging controller 41f performs the reset processing by causing the timing generator 41d to generate a reset pulse. FIG. 3 illustrates a case (reset period $P_3$) in which the imaging controller 41f resets the electric charges accumulated by the light receiving unit 41g every four frames. However, this is a mere example. For example, the frame rate can be 30 fps, and the reset cycle Tr can be about 0.5 s (the reset is performed about every 15 frames).

Figure 4:
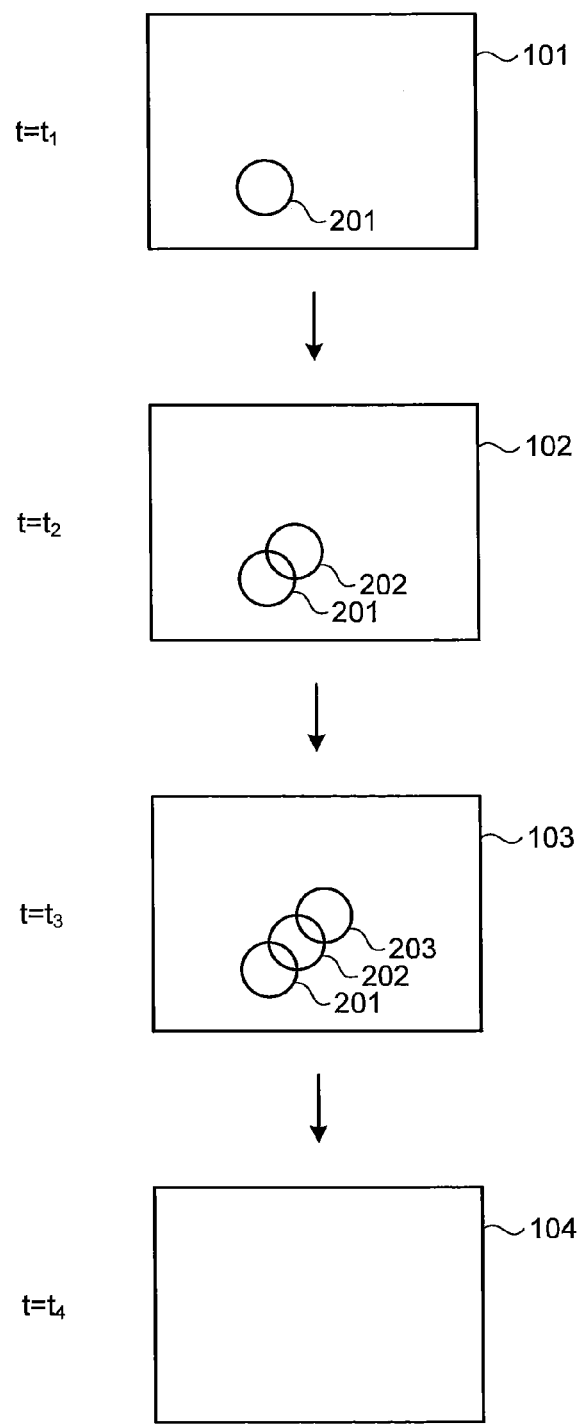
FIG. 4 is a schematic diagram illustrating a temporal change example of images captured by the endoscope system according to the first embodiment of the present invention.

FIG. 4 is a schematic diagram illustrating a temporal change example of images captured by the endoscope system 1. A time $t_i$ (i=1 to 4) corresponding to each image corresponds to a time $t_i$ illustrated in FIG. 3. FIG. 4 schematically illustrates change of a fluorescence image of when the insertion unit 2 is moved in a body at nearly the same speed. In a fluorescence image 101 at a time $t=t_1$, a fluorescent image 201 appears. In a fluorescence image 102 at a time $t=t_2$, the fluorescent image 201 that has appeared in the fluorescence image 101 appears, in addition to a fluorescent image 202. In a fluorescence image 103 at a time $t=t_3$, the fluorescent images 201 and 202 having appeared in the fluorescence image 102 appear, in addition to a fluorescent image 203. In a fluorescence image 104 at a time $t=t_4$, all of the fluorescent images appeared until then has gone. Note that the fluorescence images 101 to 104 are images in which a portion other than the fluorescent image is dark, and only a portion of the fluorescent image emits dim light.

The reason why the fluorescent image 201 having appeared in the fluorescence image 101 acquired before then appears in the fluorescence image 102 is that the reset processing has not been performed between the acquisition timing of the fluorescence image 101 and the acquisition timing of the fluorescence image 102. Similarly, the reason why the fluorescent images 201 and 202 having appeared in the fluorescence image 102 acquired before then appear in the fluorescence image 103 is that the reset processing has not been performed between the acquisition timing of the fluorescence image 102 and the acquisition timing of the fluorescence image 103. In contrast, the reason why no fluorescent image appears in the fluorescence image 104 at all is that the reset processing has been performed between the acquisition timing of the fluorescence image 103 and the acquisition timing of the fluorescence image 104.

As described above, in the fluorescent image included in the fluorescence image captured during a period in which no reset processing is performed, an afterimage having a lasting effect seems to be caused.

In contrast, when the insertion unit 2 is hardly moved after the reset processing at a certain point in a case where the fluorescence image is imaged, fluorescence images in which the fluorescent image included in the captured image gradually increases brightness can be sequentially obtained during a period until the next reset processing is performed.

In the first embodiment, the electric charges accumulated in each pixel of the light receiving unit 41g are accumulated and intensified without being reset during a predetermined period, without changing the frame rate of imaging, whereby a bright image can be obtained even if the image has low luminance like a fluorescence image.

In a method of searching for a tumor such as a cancer caused in a living body, with weak light emission such as fluorescence, an examiner may miss the weak light emission. In this regard, in the first embodiment, the reset cycle Tr is made longer than the frame cycle Tf. Therefore, while the afterimage is caused when the weak light emission portion is moved, the image is blinked when the weak light emission portion stands still, so that the visibility of the weak light emission portion can be enhanced.

Further, in the first embodiment, the frame rate of an image is unchanged. Therefore, flickering of a picture is not caused like an image with a low frame rate, and unnaturalness is not caused. Further, the frame rate of an image is unchanged, and thus readout of the image is performed at similar timing to normal imaging, and processing can be continued.

According to the above-described first embodiment of the present invention, the timing of generating the reset pulses is adjusted such that at least a part of a plurality of frames of an image is included in a period between the generation of two consecutive reset pulses. It is therefore possible to acquire an image having a wide dynamic range and excellent visibility without changing the frame rate.

Second Embodiment

A second embodiment of the present invention is characterized in that generation timing of a reset pulse is changed according to brightness of an image. An endoscope system according to the second embodiment has a similar configuration to the endoscope system 1 described in the first embodiment.

In the second embodiment, a control unit 59 of a control device 5 adjusts the generation timing of the reset pulse by transmitting a reset inhibiting signal to an imaging element 41 to mask the reset pulse generated by a timing generator 41d. Therefore, an accumulation period of electric charges is determined according to the number of frames included in an active period of the reset inhibiting signal. In this sense, in the second embodiment, the control unit 59 of the control device 5 has a function of at least a part of a reset pulse controller.

Figure 5:
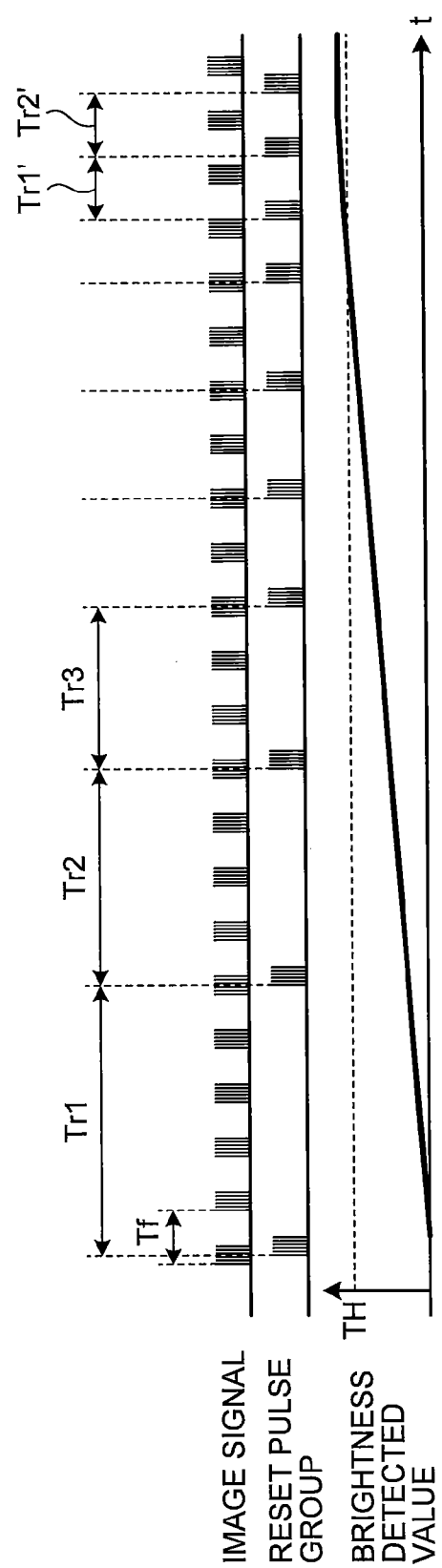
FIG. 5 is a diagram schematically illustrating a characteristic of processing performed by an endoscope system according to a second embodiment of the present invention.

FIG. 5 is a diagram schematically illustrating characteristics of processing performed by an endoscope system 1 according to the second embodiment. The endoscope system 1 is moved onto a system (electronic shutter mode) in which the reset pulse is generated in each frame while timing in one frame period is changed, when a brightness detected value is larger than a predetermined threshold, and brightness of an image can be sufficiently secured. Hereinafter, a mode different from the electronic shutter mode, and in which the entire exposure period $P_1$ of at least one frame is included in a period in which two reset pulses having a continuous generation order are generated is called long-time accumulation mode. In the case illustrated in FIG. 5, a reset cycle is gradually shorter as an increase in a brightness detected value (Tr1, Tr2, Tr3, . . . ). Then, when the brightness detected value exceeds a threshold TH, the endoscope system 1 is moved from the long-time accumulation mode to the electronic shutter mode (the reset cycle is Tr1', Tr2', . . . ).

Figure 6:
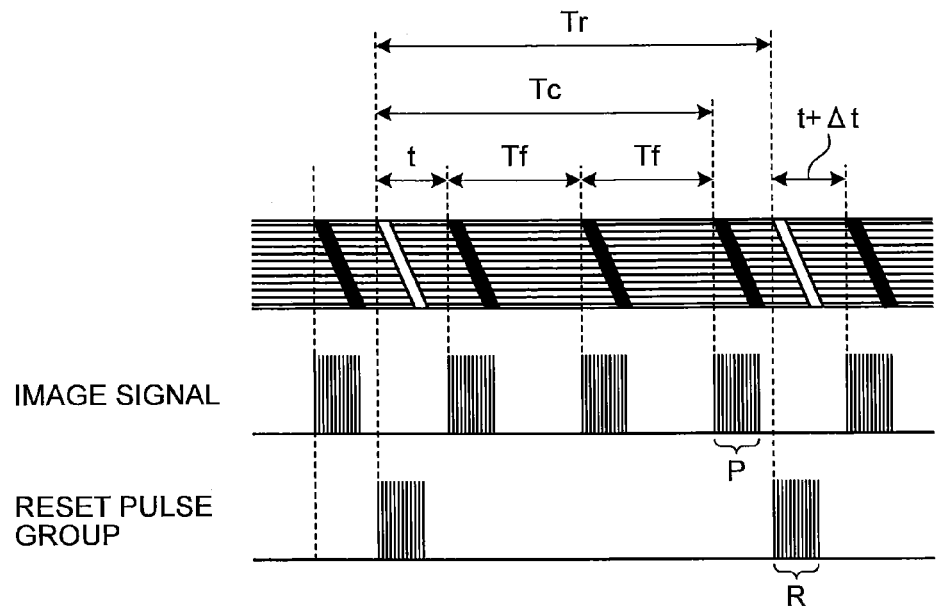
FIG. 6 is a diagram illustrating a relationship between reset timing and an exposure time in a long-time accumulation mode in more detail.

FIG. 6 is a diagram illustrating a relationship between reset timing and an exposure time in the long-time accumulation mode in more detail. An accumulation time Tc of the electric charges in the long-time accumulation mode is expressed by:

$$Tc = a \cdot Tf + t \quad (1)$$

using the number of frames (the number of total exposure frames) a in which exposure is continuously performed within the frame cycle Tf, and a time t from start of reset to start of readout in an exposure start frame. FIG. 6 exemplarily illustrates a case where the number of total exposure frames a is 2.

The endoscope system 1 changes the exposure time according to the brightness detected value of an image signal P read immediately after the number of total exposure frames a has passed, in a certain accumulation period ($\Delta t$ of FIG. 6). This change of the exposure time is realized by change of the reset timing with an electronic shutter. That is, the change of the exposure time is realized by generation of a reset signal R such that the time from the start of reset to the start of readout in the exposure start frame becomes $t+\Delta t$. A new accumulation period Tc' is expressed by:

$$Tc' = Tc + \Delta t \quad (2)$$

using a change amount of the exposure time. Further, a reset cycle Tr based on the time of occurrence of a previous reset signal is expressed by:

$$Tr = Tc + Tf - (t + \Delta t) = (a+1)Tf - \Delta t \quad (3)$$

Figure 7:
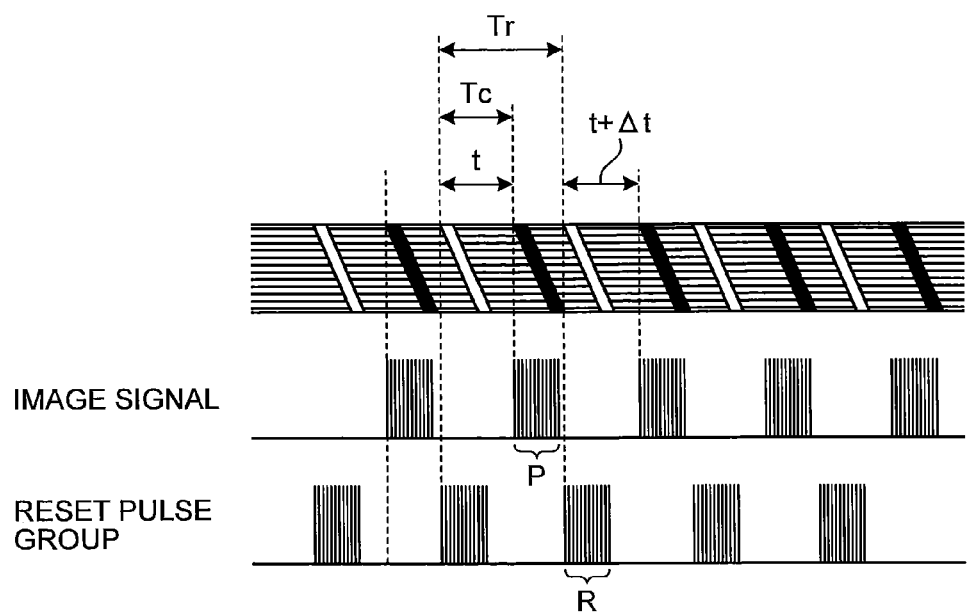
FIG. 7 is a diagram illustrating a relationship between reset timing and an exposure time in an electronic shutter mode in more detail.

FIG. 7 is a diagram illustrating a relationship between reset timing and an exposure time in the electronic shutter mode in more detail. In the electronic shutter mode, the accumulation time Tc is shorter than the frame cycle Tf, and the number of total exposure frames a is zero. Therefore, the expression (1) becomes Tc=t. It is apparent that the expressions (2) and (3) are established in the electronic shutter mode.

Note that feedback timing of the reset pulse may be determined according to the number of total exposure frames a in view of a time constant of the feedback being changed according to the value of the number of total exposure frames a. To be specific, when the number of total exposure frames a is small, the exposure time may be changed after elapse of a predetermined frame.

According to the second embodiment of the present invention, the timing of generating the reset pulses is adjusted such that at least a part of a plurality of frames of an image is included in a period between the generation of two consecutive reset pulses. It is therefore possible to acquire an image having a wide dynamic range and excellent visibility without changing the frame rate.

Further, according to the second embodiment, the time from the start of readout of an image after occurrence of the reset pulse is made variable according to the brightness information of the image, so that from the long-time exposure to the light reduction with the electronic shutter can be controlled. Accordingly, for example, in a case of fluorescence observation, observation of a fluorescent image within a visual field, and imaging of an image with high luminance after getting close to a fluorescent image can be continuously performed only by change of the generation timing of the reset pulse.

First Modification of Second Embodiment

Figure 8:
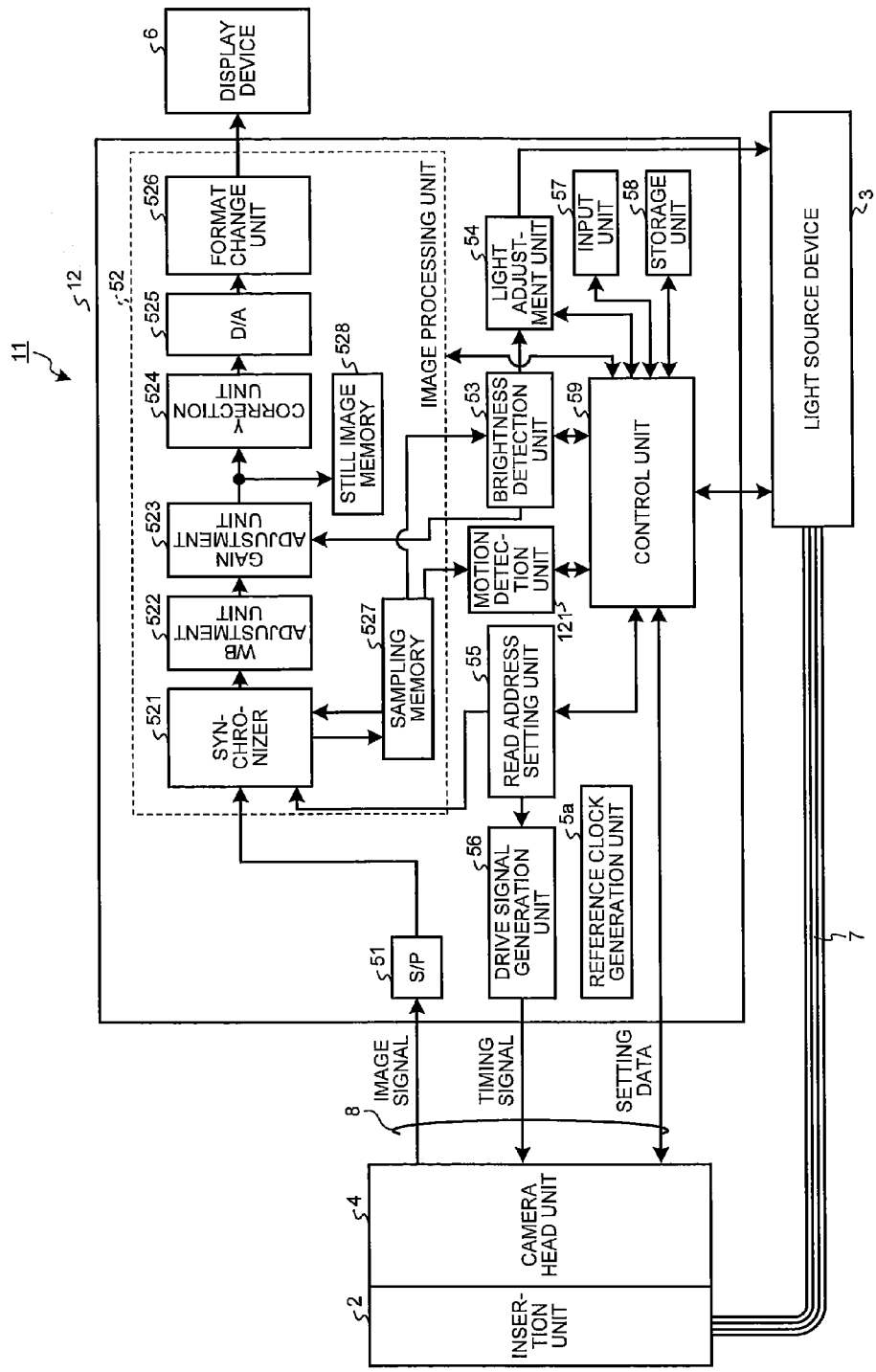
FIG. 8 is a block diagram illustrating functional configurations of principal parts of an endoscope system according to first modification of the second embodiment of the present invention.

FIG. 8 is a block diagram illustrating functional configurations of principal parts of an endoscope system according to a first modification of the second embodiment of the present invention. An endoscope system 11 illustrated in FIG. 8 is different from the endoscope system 1 in a configuration of an image processing unit.

An image processing unit 12 of the endoscope system 11 further includes a motion detection unit 121 that detects motion of an object in a plurality of frames, in addition to the configuration of the image processing unit 52 of the endoscope system 1. A control unit 59 calculates a correlation between images, based on the motion of the object detected by the motion detection unit 121, and determines generation timing of a next reset pulse, based on the calculation result and a brightness detected value. For example, when the motion of the object between fluorescence images is large (when the correlation between the images is small), the control unit 59 delays the generation timing of the reset pulse. Note that the brightness detected value also contributes to the determination of the generation timing of the reset pulse by the control unit 59. Therefore, the generation timing is not always delayed when the motion of the object is large.

According to the first modification of the second embodiment of the present invention, an afterimage of a fluorescent image is further emphasized and visibility can be enhanced, in addition to a similar effect to the second embodiment.

Second Modification of Second Embodiment

A second modification of the second embodiment of the present invention is characterized in that a control unit 59 performs control to change an accumulation time of electronic charges, when an image that satisfies a predetermined condition exists in an entire image, compared with an average value of brightness of the entire image. An endoscope system according to the second modification has a similar configuration to the endoscope system 1 described in the second embodiment.

Figure 9:
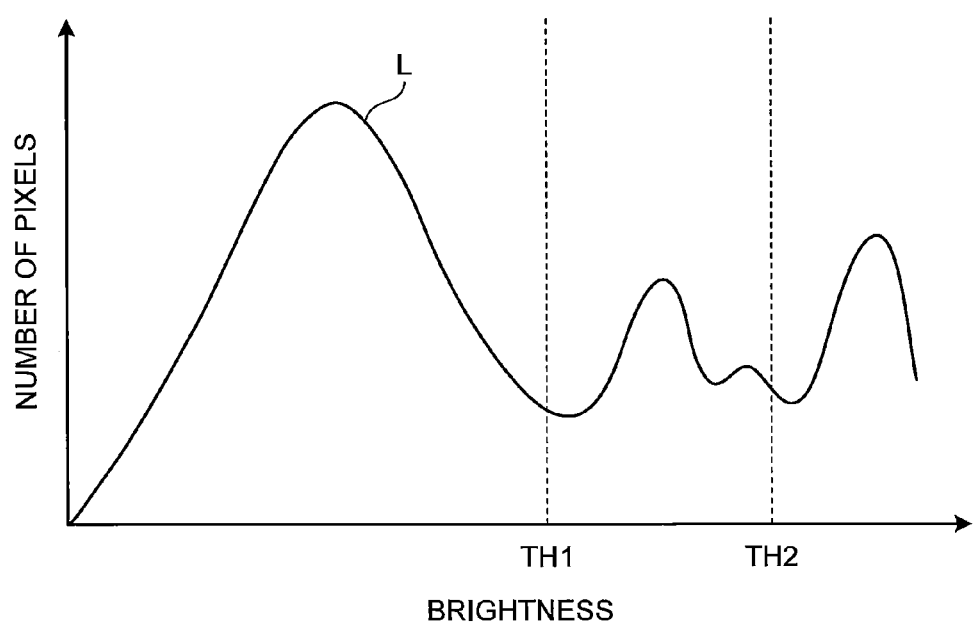
FIG. 9 is a diagram illustrating an example of a relationship between brightness (a pixel value) and the number of pixels of each brightness in an image acquired by an endoscope system according to a second modification of the second embodiment of the present invention.

FIG. 9 is a diagram illustrating an example of a relationship between brightness (pixel value) in an image acquired by an endoscope system 1 and the number of pixels of each brightness. In FIG. 9, brightness TH1 and brightness TH2 are an upper limit and a lower limit of brightness (brightness that satisfies a predetermined condition) where a difference from an average value of the brightness of the entire image falls within a predetermined range. In this sense, it is desirable that the brightness TH1 and the brightness TH2 are brightness that can eliminate a background or a noise (a stray light component) from an image to be observed (for example, a fluorescent image).

When a predetermined number or more of pixels exists, which has brightness that falls within the range of the brightness TH1 to the brightness TH2, the control unit 59 performs control to extend the accumulation time of the electric charges. Note that the control unit 59 may extend the accumulation time of the electric charges, when there is brightness that exceeds the brightness of the predetermined number of pixels in the range of the brightness TH1 to the brightness TH2.

When no image that satisfies the above-described condition exists in a read image, the endoscope system 1 performs processing described in the second embodiment.

According to the above-described second modification of the second embodiment of the present invention, the difference from the average value of the brightness of the entire image is obtained, whereby an influence of a background can be eliminated and visibility of a fluorescent image can be improved, especially in a case of a fluorescence image.

Third Embodiment

Figure 10:
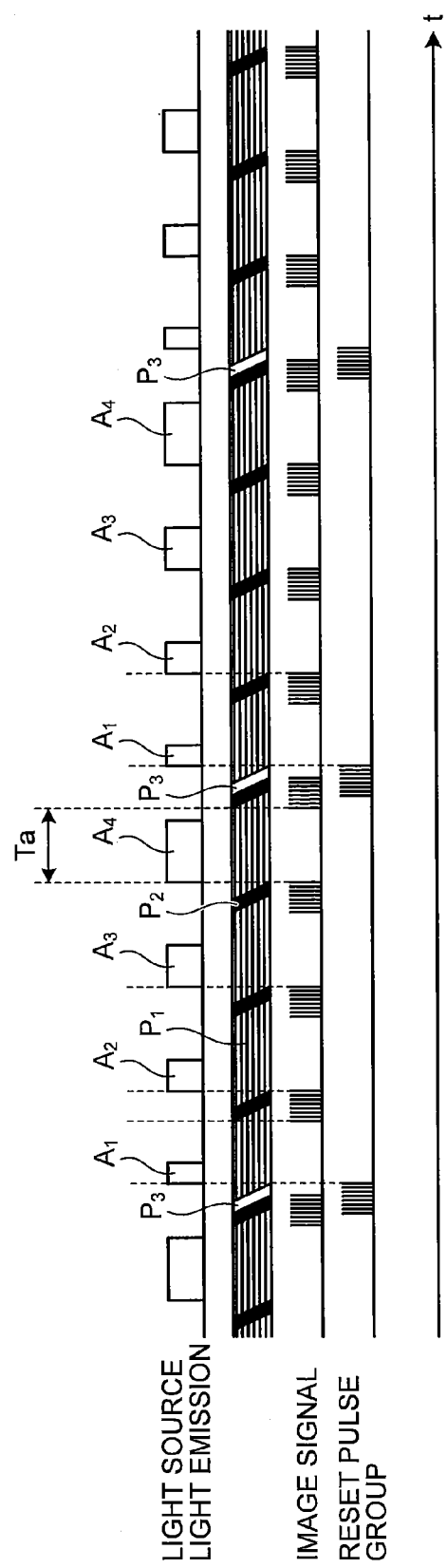
FIG. 10 is a diagram schematically illustrating an outline of an image acquisition method performed by an endoscope system according to a third embodiment of the present invention.

FIG. 10 is a diagram schematically illustrating an outline of an image acquisition method performed by an endoscope system according to a third embodiment of the present invention. Note that the endoscope system according to the third embodiment has a similar functional configuration to the endoscope system 1 described in the second embodiment. In the third embodiment, an endoscope system 1 is characterized in that illumination intensity of each frame is changed such that an afterimage or pulsation of an image in an acquired image is enhanced.

As illustrated in FIG. 10, a light source device 3 cyclically changes a light emission time while keeping light emission intensity constant, in cooperation with a control device 5, during a certain period in which all of horizontal lines of a light receiving unit 41g are in an exposure state. To be specific, a light source controller 33 of the light source device 3 performs control to make the light emission time of each frame gradually longer while keeping the light emission intensity constant, in cooperation with a control unit 59 of the control device 5. A maximum value of the light emission time is equal to or less than a length Ta of the period in which all of horizontal lines are in an exposure state.

The light source device 3 resets the light emission time of each frame to an initial value (a shortest light emission period), after accumulation of electric charges in the light receiving unit 41g is reset by a reset pulse. FIG. 10 exemplarily illustrates a case in which four light source light emission states $A_1$, $A_2$, $A_3$, and $A_4$ in which the light emission time becomes longer in this order are employed as a light source light emission state of each frame.

As described above, when the light emission time of the light source of each frame is made gradually longer in a plurality of frames included between two continuous reset processing periods, fluorescent images are gradually brighter in order of fluorescent images 201, 202, and 203, in a case illustrated in FIG. 4, for example. Therefore, visibility of the fluorescent images can be further improved.

Note that, contrary to the case illustrated in FIG. 10, the light emission time of each frame may be made gradually shorter in the plurality of frames included between the two continuous reset processing periods. In this case, the fluorescent images are gradually darker in order of the fluorescent images 201, 202, and 203 in FIG. 4, and the visibility can be improved as a result.

Further, the light emission time of the light source of each frame is not necessarily increased or decreased on a constant basis in the plurality of frames included between the two continuous reset processing periods, and may be increased or decreased in a stepwise manner or may be changed such that the increase or the decrease is appropriately mixed.

According to the above-described third embodiment of the present invention, the timing of generating the reset pulses is adjusted such that at least a part of a plurality of frames of an image is included in a period between the generation of two consecutive reset pulses. It is therefore possible to acquire an image having a wide dynamic range and excellent visibility without changing a frame rate.

Further, according to the third embodiment, the illumination intensity of each frame of an acquired image is changed, whereby the visibility can be further improved.

Modification of Third Embodiment

Figure 11:
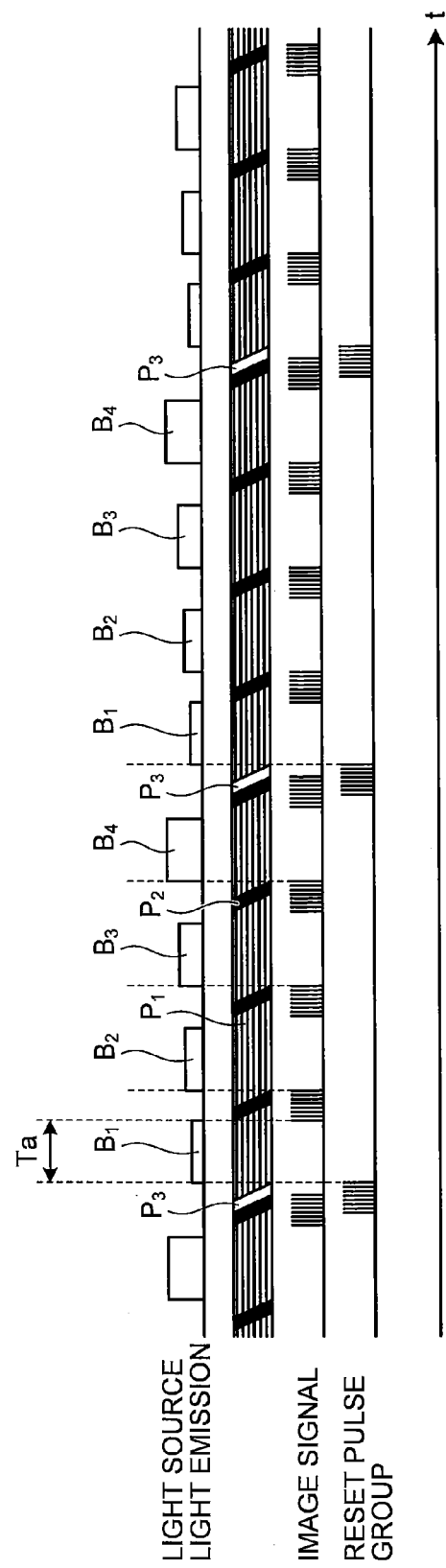
FIG. 11 is a diagram schematically illustrating an outline of an image acquisition method performed by an endoscope system according to a modification of the third embodiment of the present invention.

FIG. 11 is a diagram schematically illustrating an outline of an image acquisition method performed by an endoscope system 1 according to a modification of the third embodiment of the present invention. As illustrated in FIG. 11, a light source device 3 cyclically changes light emission intensity while keeping a light emission time of each frame constant, in a period in which all of horizontal lines of a light receiving unit 41g are in an exposure state. To be specific, the light source device 3 makes the light emission intensity of each frame gradually larger while keeping the light emission time of each frame constant. Then, after accumulation of electric charges in a light receiving unit 41g is reset by a reset signal, the light source device 3 resets the light emission intensity of each frame to an initial value (smallest light emission intensity). In FIG. 11, four light source light emission states $B_1$, $B_2$, $B_3$, and $B_4$ in which the light emission intensity becomes smaller is employed as a light source light emission state of each frame.

As described above, when the light emission intensity of the light source of each frame is gradually increased in the plurality of frames included in the two continuous reset processing periods, the visibility of the fluorescent image can be further improved, similarly to the above-described third embodiment.

Note that, in the modification, the light emission intensity may be gradually decreased while the light mission time of each frame is kept constant in the plurality of frames included in the two continuous reset processing periods.

Further, the light emission intensity of each frame is not necessarily increased or decreased on a constant basis in the plurality of frames included in the two continuous reset processing periods, and the light emission intensity may be increased or decreased in a stepwise manner, or may be changed such that the increase or the decrease is appropriately mixed.

Further, both of the light emission intensity and the light emission time may be changed by combination of the modification with the third embodiment.

Other Embodiments

Modes for carrying out the present invention have been described so far. However, the present invention should not be limited only by the above-described first to third embodiments. For example, in the first embodiment, the generation timing of the reset pulse may be adjusted by generation of the reset inhibiting signal by the control device 5, similarly to the second embodiment and the like.

In some embodiments, a gain adjustment unit of a control device may change an amplification factor of each frame in a plurality of frames included in two continuous reset processing periods. In this case, the amplification factor of each frame may be gradually increased or decreased, or may be changed such that the increase or the decrease in the amplification factor is appropriately mixed.

In some embodiments, an imaging element may include a CCD image sensor.

Further, an endoscope system according to some embodiments can be realized as a flexible mirror that is inserted into a subject and observes an inside of an organ.

According to some embodiments, timing of generating reset pulses is adjusted such that at least a part of a plurality of frames of an image is included in a period between the generation of two consecutive reset pulses. It is therefore possible to acquire an image having a wide dynamic range and excellent visibility without changing a frame rate.

As described above, the present invention may include various embodiments that are not described here, and various design chances and the like can be made within the scope of the technical idea described in claims.

REFERENCE SIGNS LIST

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an illumination unit configured to irradiate a visual field area with illumination light that produces return light from a specific substance;
   a sensor unit having a two-dimensional surface on which a plurality of pixels is arranged for receiving the return light from the visual field area and photoelectrically converting the return light to generate electrical signals, the sensor unit being configured to sequentially read out the electrical signals generated by the plurality of pixels, as image information;
   a reading unit configured to read out the electrical signals per a specified frame cycle;
   a reset pulse generation unit configured to generate reset pulses for releasing electric charges accumulated in the plurality of pixels;
   a reset pulse controller configured to adjust timing of generating the reset pulses such that a plurality of frame cycles is included in a period between generation of two consecutive reset pulses;
   an illumination controller configured to cause the illumination unit to emit the illumination light in each of the plurality of frame cycles present between the generation of one reset pulse and the generation of a next reset pulse;
   a brightness detection unit configured to detect brightness of an image included in the image information read out by the sensor unit; and
   a motion detection unit configured to detect a motion amount of an object between a plurality of frames;
   wherein the reset pulse controller is configured to adjust the timing of generating the reset pulses according to the brightness of the image detected by the brightness detection unit and the motion amount of the object detected by the motion detection unit.

2. The endoscope system according to claim 1, wherein the illumination unit is configured to change, for each frame, at least one of light emission intensity and a light emission time in one frame of the illumination light.

3. The endoscope system according to claim 1, further comprising an amplification factor adjustment unit configured to change, for each frame, an amplification factor of an image included in the image information.

* * * * *